US011798677B2

United States Patent
van der Veen et al.

(10) Patent No.: US 11,798,677 B2
(45) Date of Patent: Oct. 24, 2023

(54) METHOD AND SYSTEM FOR PROVIDING A GUIDED WORKFLOW THROUGH A SERIES OF ULTRASOUND IMAGE ACQUISITIONS WITH REFERENCE IMAGES UPDATED BASED ON A DETERMINED ANATOMICAL POSITION

(71) Applicant: GE Precision Healthcare LLC, Milwaukee, WI (US)

(72) Inventors: Lucienne van der Veen, Geinberg (AT); Christian Fritz Perrey, Mondsee (AT)

(73) Assignee: GE PRECISION HEALTHCARE LLC, Milwaukee, WI (US)

(*) Notice: Subject to any disclaimer, the term of this patent is extended or adjusted under 35 U.S.C. 154(b) by 659 days.

(21) Appl. No.: 16/731,730

(22) Filed: Dec. 31, 2019

(65) Prior Publication Data
US 2021/0202069 A1 Jul. 1, 2021

(51) Int. Cl.
*G16H 30/20* (2018.01)
*G06T 3/60* (2006.01)
(Continued)

(52) U.S. Cl.
CPC ............... *G16H 30/20* (2018.01); *G06T 3/60* (2013.01); *G06T 7/0012* (2013.01); *G06T 7/70* (2017.01);
(Continued)

(58) Field of Classification Search
CPC ........ G16H 30/20; G16H 30/40; G16H 40/63; G16H 50/20; G16H 50/30; G16H 30/00; G16H 40/67; G16H 10/60; G16H 50/50; G16H 50/70; G06T 3/60; G06T 7/0012; G06T 7/70; G06T 2207/10132; G06T 2207/20101; G06T 2207/30012;
(Continued)

(56) References Cited

U.S. PATENT DOCUMENTS

2009/0012432 A1* 1/2009 Sharf .................... A61B 5/1116
600/588
2011/0295120 A1 12/2011 Lee
(Continued)

*Primary Examiner* — Nimesh Patel
(74) *Attorney, Agent, or Firm* — McAndrews, Held & Malloy, Ltd.; Jacob Groethe; David Bates

(57) ABSTRACT

A system and method for providing a guided workflow through a series of ultrasound image acquisitions with reference images updated based on a determined anatomical position is provided. The method includes acquiring and displaying, by an ultrasound system, at least one ultrasound image of an anatomy. The method includes determining, by at least one processor, a position of the anatomy depicted in the at least one ultrasound image. The method includes automatically selecting and displaying, by the at least one processor, reference images corresponding to pre-defined views of an ultrasound examination. An orientation of anatomy depicted in the selected and displayed reference images is based on the determined position of the anatomy. The method includes acquiring and displaying, by the ultrasound system, additional ultrasound images of the anatomy corresponding to the selected and displayed reference images. The additional ultrasound images include pre-defined views of the ultrasound examination.

20 Claims, 6 Drawing Sheets

(51) Int. Cl.
*G06T 7/00* (2017.01)
*G06T 7/70* (2017.01)

(52) U.S. Cl.
CPC ............... *G06T 2207/10132* (2013.01); *G06T 2207/20101* (2013.01); *G06T 2207/30012* (2013.01); *G06T 2207/30044* (2013.01)

(58) Field of Classification Search
CPC . G06T 2207/30044; G06T 2207/20081; G06T 2207/20084; G06T 2207/10136; G06T 7/73; G06T 2207/30048; G06T 2200/04; G06T 2207/10016; G06T 2207/30004; G06T 7/0014; G06T 2207/30008; G06T 11/001; G06T 2207/10088; G06T 2219/2016; G06T 2207/10028; G06T 7/00; G06T 7/149; G06T 2207/20116; G06T 7/12; A61B 8/0866; A61B 8/463; A61B 8/52; A61B 8/523; A61B 8/08; A61B 5/0205; A61B 5/742; A61B 5/02055; A61B 5/0215; A61B 5/318; A61B 2503/045; A61B 5/05; A61B 1/303; A61B 1/05; A61B 5/035; A61B 5/4343; A61B 5/02; A61B 5/4094; G06F 16/40; G06F 3/011; G06F 3/012; G06F 3/013; G06F 3/017; G06F 3/0482; G06F 3/0484; G06F 3/04845; G06N 3/08; G06N 3/0454; G06N 20/00; G06N 20/10; G06N 7/005

See application file for complete search history.

(56) References Cited

U.S. PATENT DOCUMENTS

| | | | |
|---|---|---|---|
| 2016/0374644 A1* | 12/2016 | Mauldin, Jr. | A61B 8/085 600/424 |
| 2018/0189992 A1* | 7/2018 | Pelissier | G16H 40/63 |
| 2019/0057620 A1* | 2/2019 | Eggert | G09B 5/14 |
| 2020/0113544 A1* | 4/2020 | Huepf | G06T 7/0012 |

* cited by examiner

METHOD AND SYSTEM FOR PROVIDING A GUIDED WORKFLOW THROUGH A SERIES OF ULTRASOUND IMAGE ACQUISITIONS WITH REFERENCE IMAGES UPDATED BASED ON A DETERMINED ANATOMICAL POSITION

FIELD

Certain embodiments relate to ultrasound imaging. More specifically, certain embodiments relate to a method and system for providing an assisted workflow through a series of ultrasound image acquisitions. The system may present reference images corresponding to each image view to be acquired. The reference images may be presented based on a determined position of the target anatomy.

BACKGROUND

Ultrasound imaging is a medical imaging technique for imaging organs and soft tissues in a human body. Ultrasound imaging uses real time, non-invasive high frequency sound waves to produce two-dimensional (2D), three-dimensional (3D), and/or four-dimensional (4D) (i.e., real-time/continuous 3D images) images.

Ultrasound imaging is a valuable, non-invasive tool for diagnosing various medical conditions. Acquired ultrasound data may be analyzed and/or processed to visualize anatomical structures evaluated by a medical professional to perform the diagnosis. Typical ultrasound examinations are performed by acquiring a series of ultrasound images in different planes. In some cases, such as when scanning a fetus, the acquired images may change significantly based on the fetal lie and orientation. Accordingly, less experienced ultrasound operators, such as an obstetrician, may have difficulty acquiring several of the image views for performing a diagnosis. For example, a fetal congenital heart disease ultrasound examination may involve acquiring a four chamber (4CH) view, a three vessel and trachea (3VT) view, left ventricular and right ventricular outflow tract views, short axis views (low for ventricles and high for outflow tracts), a long axis view, an aortic arch view, a ductal arch view, and superior and inferior vena cava views. Although an inexperience ultrasound operator may be able to manipulate the ultrasound probe to obtain some of the views, many other views may be difficult to obtain. Thus, in many cases, congenital heart disease in fetal ultrasound may go undetected.

Further limitations and disadvantages of conventional and traditional approaches will become apparent to one of skill in the art, through comparison of such systems with some aspects of the present disclosure as set forth in the remainder of the present application with reference to the drawings.

BRIEF SUMMARY

A system and/or method is provided for a guided workflow through a series of ultrasound image acquisitions with reference images updated based on a determined anatomical position, as set forth more completely in the claims.

These and other advantages, aspects and novel features of the present disclosure, as well as details of an illustrated embodiment thereof, will be more fully understood from the following description and drawings.

DETAILED DESCRIPTION

Figure 1:
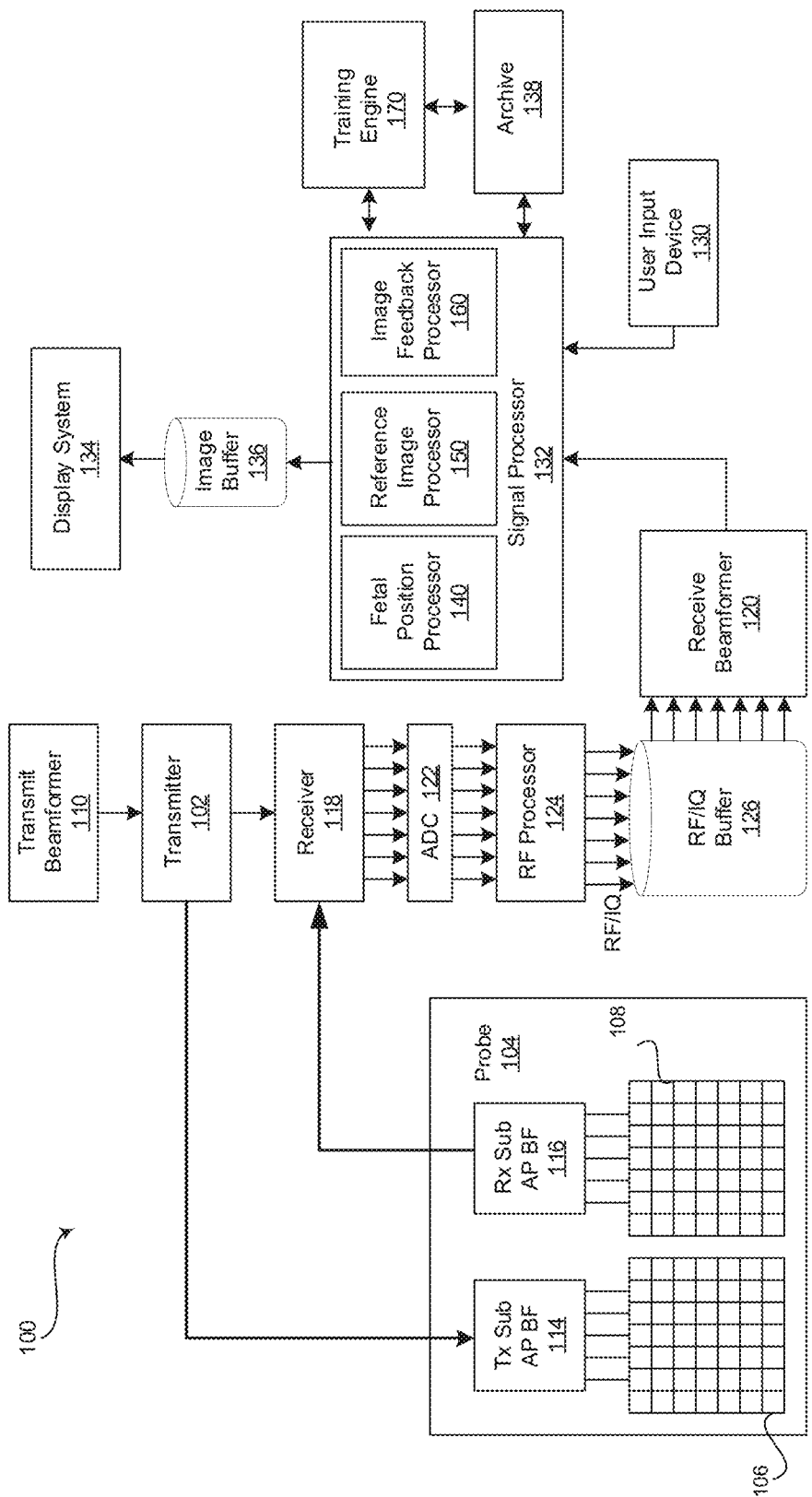
FIG. 1 is a block diagram of an exemplary ultrasound system that is operable to provide a guided workflow through a series of ultrasound image acquisitions with reference images updated based on a determined anatomical position, in accordance with various embodiments.

Certain embodiments may be found in a method and system for providing a guided workflow through a series of ultrasound image acquisitions with reference images updated based on a determined anatomical position. Various embodiments have the technical effect of presenting reference images of a particular anatomical structure having a position and orientation corresponding with the position and orientation of the anatomical structure acquired via an ultrasound system. Aspects of the present have the technical effect of automatically selecting and/or rotating the reference images based on a determined anatomical position and presenting the reference images to an ultrasound operator to assist acquisition of predetermined ultrasound views.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general-purpose signal processor or a block of random access memory, hard disk, or the like) or multiple pieces of hardware. Similarly, the programs may be stand-alone programs, may be incorporated as subroutines in an operating system, may be functions in an installed software package, and the like. It should be understood that the various embodiments are not limited to the arrangements and instrumentality shown in the drawings. It should also be understood that the embodiments may be combined, or that other embodiments may be utilized and that structural, logical and electrical changes may be made without departing from the scope of the various embodiments. The following detailed description is, therefore, not to be taken in a limiting sense, and the scope of the present disclosure is defined by the appended claims and their equivalents.

As used herein, an element or step recited in the singular and preceded with the word "a" or "an" should be understood as not excluding plural of said elements or steps, unless such exclusion is explicitly stated. Furthermore, references to "an exemplary embodiment," "various embodiments," "certain embodiments," "a representative embodiment," and the like are not intended to be interpreted as excluding the existence of additional embodiments that also incorporate the recited features. Moreover, unless explicitly stated to the contrary, embodiments "comprising," "including," or "having" an element or a plurality of elements having a particular property may include additional elements not having that property.

Also as used herein, the term "image" broadly refers to both viewable images and data representing a viewable image. However, many embodiments generate (or are configured to generate) at least one viewable image. In addition, as used herein, the phrase "image" is used to refer to an ultrasound mode such as B-mode (2D mode), M-mode, three-dimensional (3D) mode, CF-mode, PW Doppler, CW Doppler, MGD, and/or sub-modes of B-mode and/or CF such as Shear Wave Elasticity Imaging (SWEI), TVI, Angio, B-flow, BMI, BMI_Angio, and in some cases also MM, CM, TVD where the "image" and/or "plane" includes a single beam or multiple beams.

Furthermore, the term processor or processing unit, as used herein, refers to any type of processing unit that can carry out the required calculations needed for the various embodiments, such as single or multi-core: CPU, Accelerated Processing Unit (APU), Graphics Board, DSP, FPGA, ASIC or a combination thereof.

Although the exemplary embodiments described below are presented with respect to the acquisition of ultrasound images of a fetus for diagnosing congenital heart disease, the disclosure is not limited to fetal ultrasound and congenital heart examinations. Instead, aspects of the present disclosure are applicable to ultrasound examinations of any suitable anatomical structure for diagnosing any suitable condition.

It should be noted that various embodiments described herein that generate or form images may include processing for forming images that in some embodiments includes beamforming and in other embodiments does not include beamforming. For example, an image can be formed without beamforming, such as by multiplying the matrix of demodulated data by a matrix of coefficients so that the product is the image, and wherein the process does not form any "beams". Also, forming of images may be performed using channel combinations that may originate from more than one transmit event (e.g., synthetic aperture techniques).

In various embodiments, ultrasound processing to form images is performed, for example, including ultrasound beamforming, such as receive beamforming, in software, firmware, hardware, or a combination thereof. One implementation of an ultrasound system having a software beamformer architecture formed in accordance with various embodiments is illustrated in FIG. 1.

FIG. 1 is a block diagram of an exemplary ultrasound system that is operable to provide a guided workflow through a series of ultrasound image acquisitions with reference images updated based on a determined anatomical position, in accordance with various embodiments. Referring to FIG. 1, there is shown an ultrasound system 100. The ultrasound system 100 comprises a transmitter 102, an ultrasound probe 104, a transmit beamformer 110, a receiver 118, a receive beamformer 120, A/D converters 122, a RF processor 124, a RF/IQ buffer 126, a user input device 130, a signal processor 132, an image buffer 136, a display system 134, an archive 138, and a training engine 170.

The transmitter 102 may comprise suitable logic, circuitry, interfaces and/or code that may be operable to drive an ultrasound probe 104. The ultrasound probe 104 may comprise a two dimensional (2D) array of piezoelectric elements. The ultrasound probe 104 may comprise a group of transmit transducer elements 106 and a group of receive transducer elements 108, that normally constitute the same elements. In certain embodiment, the ultrasound probe 104 may be operable to acquire ultrasound image data covering at least a substantial portion of an anatomy, such as a fetus, a spine, an endometrium of a uterus, a heart, a blood vessel, or any suitable anatomical structure.

The transmit beamformer 110 may comprise suitable logic, circuitry, interfaces and/or code that may be operable to control the transmitter 102 which, through a transmit sub-aperture beamformer 114, drives the group of transmit transducer elements 106 to emit ultrasonic transmit signals into a region of interest (e.g., human, animal, underground cavity, physical structure and the like). The transmitted ultrasonic signals may be back-scattered from structures in the object of interest, like blood cells or tissue, to produce echoes. The echoes are received by the receive transducer elements 108.

The group of receive transducer elements 108 in the ultrasound probe 104 may be operable to convert the received echoes into analog signals, undergo sub-aperture beamforming by a receive sub-aperture beamformer 116 and are then communicated to a receiver 118. The receiver 118 may comprise suitable logic, circuitry, interfaces and/or code that may be operable to receive the signals from the receive sub-aperture beamformer 116. The analog signals may be communicated to one or more of the plurality of A/D converters 122.

The plurality of A/D converters 122 may comprise suitable logic, circuitry, interfaces and/or code that may be operable to convert the analog signals from the receiver 118 to corresponding digital signals. The plurality of A/D converters 122 are disposed between the receiver 118 and the RF processor 124. Notwithstanding, the disclosure is not limited in this regard. Accordingly, in some embodiments, the plurality of A/D converters 122 may be integrated within the receiver 118.

The RF processor 124 may comprise suitable logic, circuitry, interfaces and/or code that may be operable to demodulate the digital signals output by the plurality of A/D converters 122. In accordance with an embodiment, the RF processor 124 may comprise a complex demodulator (not shown) that is operable to demodulate the digital signals to form I/Q data pairs that are representative of the corresponding echo signals. The RF or I/Q signal data may then be communicated to an RF/IQ buffer 126. The RF/IQ buffer 126 may comprise suitable logic, circuitry, interfaces and/or code that may be operable to provide temporary storage of the RF or I/Q signal data, which is generated by the RF processor 124.

The receive beamformer 120 may comprise suitable logic, circuitry, interfaces and/or code that may be operable to perform digital beamforming processing to, for example, sum the delayed channel signals received from RF processor 124 via the RF/IQ buffer 126 and output a beam summed signal. The resulting processed information may be the beam summed signal that is output from the receive beamformer 120 and communicated to the signal processor 132. In accordance with some embodiments, the receiver 118, the plurality of A/D converters 122, the RF processor 124, and the beamformer 120 may be integrated into a single beamformer, which may be digital. In various embodiments, the ultrasound system 100 comprises a plurality of receive beamformers 120.

The user input device 130 may be utilized to input patient data, scan parameters, settings, select protocols and/or templates, answer system prompts regarding the appearance of anatomical structures in acquired ultrasound images, and the like. In an exemplary embodiment, the user input device 130 may be operable to configure, manage and/or control operation of one or more components and/or modules in the ultrasound system 100. In this regard, the user input device 130 may be operable to configure, manage and/or control operation of the transmitter 102, the ultrasound probe 104, the transmit beamformer 110, the receiver 118, the receive beamformer 120, the RF processor 124, the RF/IQ buffer 126, the user input device 130, the signal processor 132, the image buffer 136, the display system 134, the archive 138, and/or the training engine 170. The user input device 130 may include button(s), rotary encoder(s), a touchscreen, a touch pad, a trackball, motion tracking, voice recognition, a mousing device, keyboard, camera and/or any other device capable of receiving a user directive. In certain embodiments, one or more of the user input devices 130 may be integrated into other components, such as the display system 134, for example. As an example, user input device 130 may include a touchscreen display.

In various embodiments, the user input device 130 may be operable to select an examination type having an associated protocol defining image views for acquisition. For example, a user may select a fetal congenital heart disease ultrasound examination or any suitable examination type. The selected examination type may be associated with a number of defined image views for acquisition. For example, in the case of a fetal congenital heart disease ultrasound examination, the examination may be associated with a four chamber (4CH) view, a three vessel and trachea (3VT) view, left ventricular and right ventricular outflow tract views, short axis views (low for ventricles and high for outflow tracts), a long axis view, an aortic arch view, a ductal arch view, superior and inferior vena cava views, and/or any suitable views. In an exemplary embodiment, the user input device 130 may be operable to provide selections and/or answers regarding a position and/or orientation of a target anatomical structure depicted in one or more ultrasound images. For example, in the case of a fetal congenital heart disease ultrasound examination, the user input device 130 may be used to provide selection or answers to system prompts with respect to a fetal lie and a spine position. As an example, the user input device 130 may be used select a cephalic lie or a breech lie. As another example, the user input device 130 may be used to select an indication of a spine position in an ultrasound image, such as spine at 3 o'clock (or 90 degrees), spine at 4 o'clock (or 120 degrees), spine at 5 o'clock (or 150 degrees), spine at 6 o'clock (or 180 degrees), spine at 7 o'clock (or 210 degrees), spine at 8 o'clock (or 240 degrees), spine at 9 o'clock (or 270 degrees), and/or any suitable spine position identifier. In various embodiments, the user input device 130 may be operable to provide selections and/or answers to system prompts regarding the appearance of the presented ultrasound images in comparison with presented reference images. For example, in the case of a 4CH view in a fetal congenital heart disease ultrasound examination, the user input device 130 may be operable to select and/or answer whether the apex points to the fetal left. As another example, the user input device 130 may be operable to select and/or answer whether the orientation, size, and/or configuration of the structures in an acquired image match the reference image.

The signal processor 132 may comprise suitable logic, circuitry, interfaces and/or code that may be operable to process ultrasound scan data (i.e., summed IQ signal) for generating ultrasound images for presentation on a display system 134. The signal processor 132 is operable to perform one or more processing operations according to a plurality of selectable ultrasound modalities on the acquired ultrasound scan data. In an exemplary embodiment, the signal processor 132 may be operable to perform display processing and/or control processing, among other things. Acquired ultrasound scan data may be processed in real-time during a scanning session as the echo signals are received. Additionally or alternatively, the ultrasound scan data may be stored temporarily in the RF/IQ buffer 126 during a scanning session and processed in less than real-time in a live or off-line operation. In various embodiments, the processed image data can be presented at the display system 134 and/or may be stored at the archive 138. The archive 138 may be a local archive, a Picture Archiving and Communication System (PACS), or any suitable device for storing images and related information.

The signal processor 132 may be one or more central processing units, microprocessors, microcontrollers, and/or the like. The signal processor 132 may be an integrated component, or may be distributed across various locations, for example. In an exemplary embodiment, the signal processor 132 may comprise a fetal position processor 140, a reference image processor 150, and an image feedback processor 160. The signal processor 132 may be capable of receiving input information from a user input device 130 and/or archive 138, generating an output displayable by a display system 134, and manipulating the output in response to input information from a user input device 130, among other things. The signal processor 132, including the fetal position processor 140 the reference image processor 150, and the image feedback processor 160, may be capable of executing any of the method(s) and/or set(s) of instructions discussed herein in accordance with the various embodiments, for example.

The ultrasound system 100 may be operable to continuously acquire ultrasound scan data at a frame rate that is suitable for the imaging situation in question. Typical frame rates range from 20-120 but may be lower or higher. The acquired ultrasound scan data may be displayed on the display system 134 at a display-rate that can be the same as the frame rate, or slower or faster. An image buffer 136 is included for storing processed frames of acquired ultrasound scan data that are not scheduled to be displayed immediately. Preferably, the image buffer 136 is of sufficient capacity to store at least several minutes' worth of frames of ultrasound scan data. The frames of ultrasound scan data are stored in a manner to facilitate retrieval thereof according to its order or time of acquisition. The image buffer 136 may be embodied as any known data storage medium.

Figure 2:
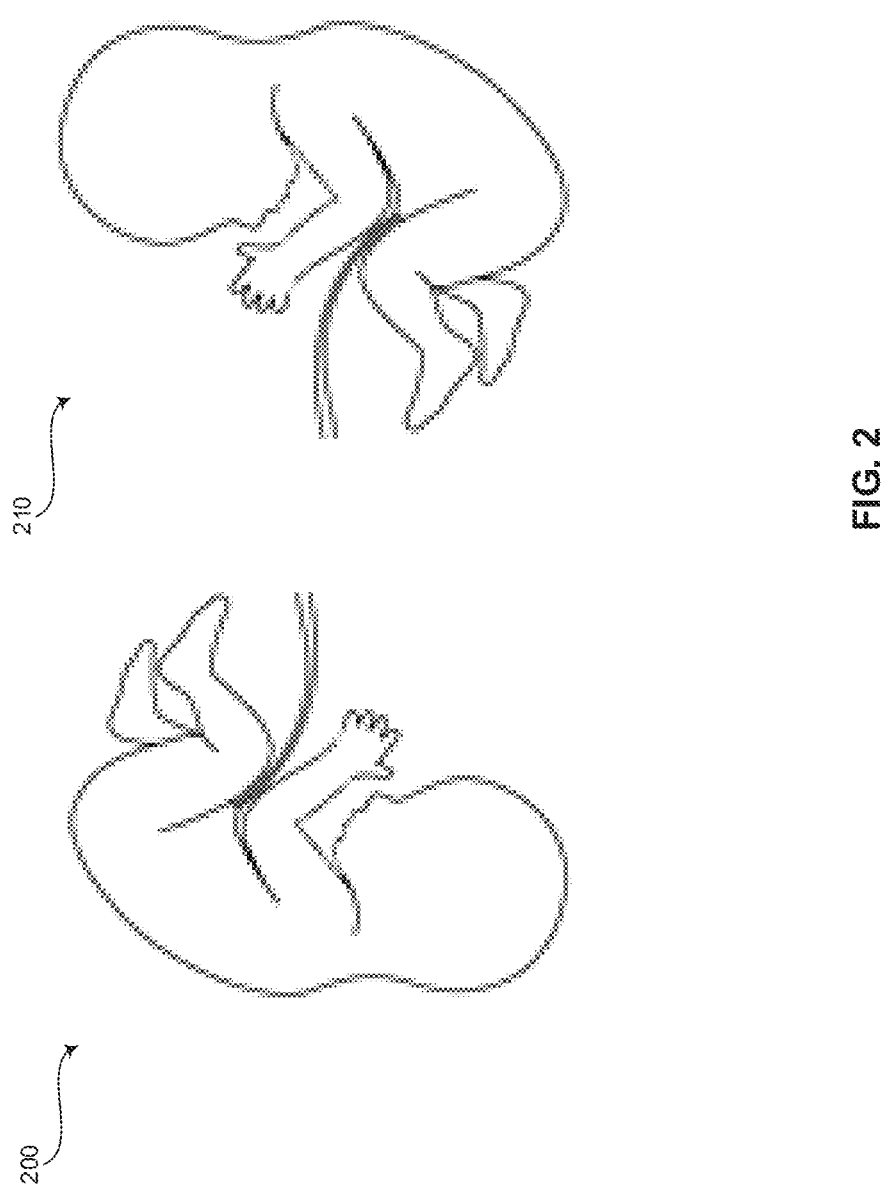
FIG. 2 is a display of exemplary fetal lies, in accordance with various embodiments.

The signal processor 132 may include a fetal position processor 140 that comprises suitable logic, circuitry, interfaces and/or code that may be operable to determine a fetal position. For example, the fetal position processor 140 may determine the fetal position based on a fetal lie and spine position, or any suitable fetal characteristic or combination of fetal characteristics. The fetal characteristics may be provided via automatic or manual detection. For example, an ultrasound operator may acquire an ultrasound image of a fetal head, spine, and/or legs. In various embodiments, the fetal position processor 140 and/or reference image processor 150 may optionally provide reference images showing a reference fetal head, spine, and/or legs in different positions, such as cephalic and breech positions. FIG. 2 is a display of exemplary fetal lies 200, 210, in accordance with various embodiments. Referring to FIG. 2, a fetus may lie in a cephalic position 200 or a breech position 210, for example. Referring again to FIG. 1, the fetal position processor 140 may be configured to manually select the fetal lie, such as based on a user instruction via the user input device 130. For example, the ultrasound operator may provide a user instruction via the user input device 130 to the fetal position processor 140 to select a cephalic lie based on analysis by the operator of the acquired ultrasound image of the fetal head, spine, and/or legs. As an example, a user may provide a voice command, probe gesture, button depression, touchscreen input, or the like that instructs the fetal position processor 140 to select a cephalic lie. In various embodiments, the operator may perform the analysis based on the acquired ultrasound image of the fetal head, spine, and/or legs alone, or in comparison with one or more reference images, such as a cephalic lie reference image and a breech reference image.

Figure 3:
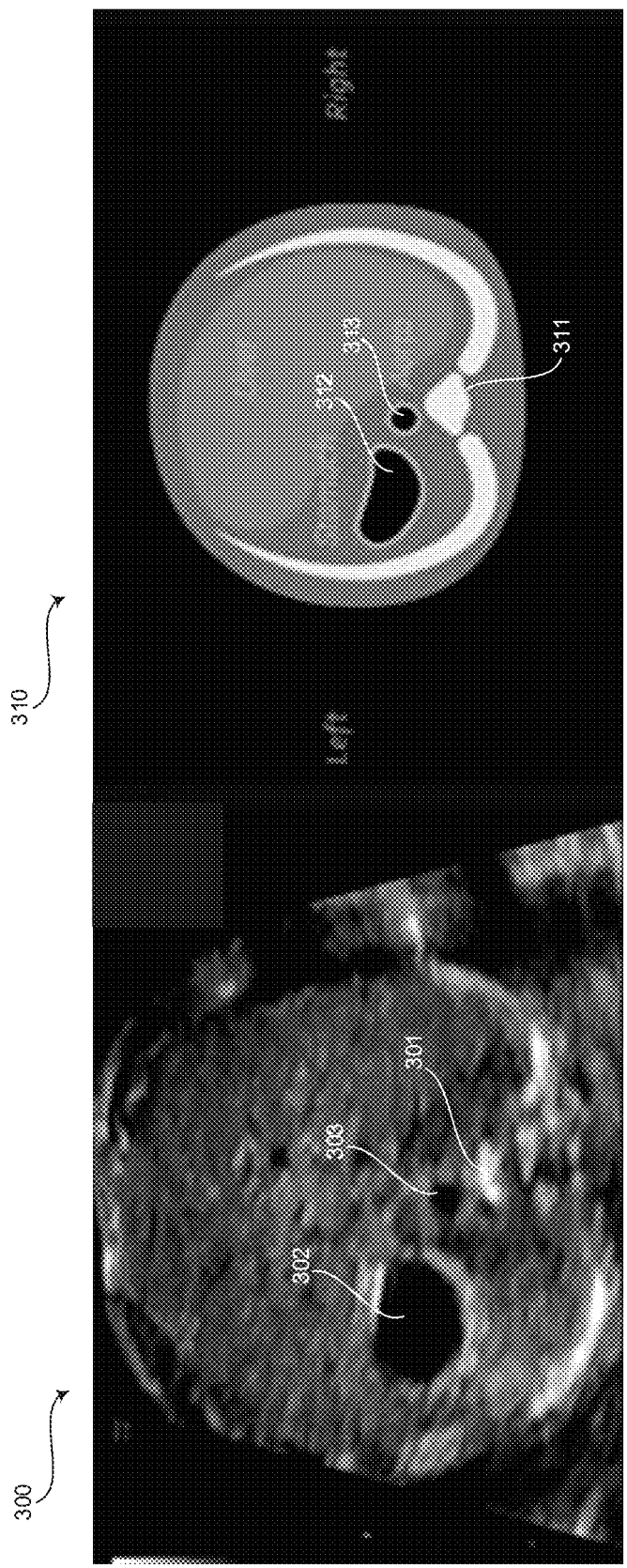
FIG. 3 is an exemplary display of an ultrasound image and reference image that may be used to determine a fetal spine position, in accordance with various embodiments.

The fetal position processor 140 may be configured to manually select the spine position, such as based on a user instruction via the user input device 130. For example, the ultrasound operator may provide a user instruction via the user input device 130 to the fetal position processor 140 to select a 6 o'clock (180 degrees) spine position based on analysis by the operator of the acquired ultrasound image of the fetal spine. As an example, a user may provide a voice command, probe gesture, button depression, touchscreen input, or the like that instructs the fetal position processor 140 to select a 6 o'clock (180 degrees) spine position. In various embodiments, the operator may perform the analysis based on the acquired ultrasound image of the fetal spine alone, or in comparison with one or more reference images, such as images of the spine at 3 o'clock (or 90 degrees), spine at 4 o'clock (or 120 degrees), spine at 5 o'clock (or 150 degrees), spine at 6 o'clock (or 180 degrees), spine at 7 o'clock (or 210 degrees), spine at 8 o'clock (or 240 degrees), spine at 9 o'clock (or 270 degrees), and/or any suitable spine position identifier. FIG. 3 is an exemplary display of an ultrasound image 300 and reference image 310 that may be used to determine a fetal spine position, in accordance with various embodiments. Referring to FIG. 3, a transverse abdominal view showing a cross-section of the thorax of a fetus may be acquired by the ultrasound system 100 and presented at display system 134 with a reference image 310. The reference image 310 may be a pictogram as shown in FIG. 3 or a pre-acquired ultrasound image, for example. The ultrasound operator may reference the reference image(s) 310 when manipulating the ultrasound probe 104 to confirm the appropriate viewing plan is acquired. The reference image 310 of FIG. 3 shows the spine 311 at 6 o'clock (180 degrees). The reference image(s) 310 may include additional anatomical structures, such as ribs, the stomach 312, the aorta 313, and the liver, among other things, to assist identifying the appropriate plane. In various embodiments, the anatomical structures of the reference image(s) 310 may be labeled as shown in FIG. 3. In certain embodiments, additional reference images 310 may be presented with the anatomical structures 311-313 oriented differently, such as spine at 3 o'clock (or 90 degrees), spine at 4 o'clock (or 120 degrees), etc. as discussed above. The acquired ultrasound image 300 depicts a substantially similar view as the reference image 310 and includes the spine 301, stomach 302, and aorta 303 positioned at a substantially same orientation as the anatomical structures 311-313 depicted in the reference image 310. Accordingly, the ultrasound operator may confirm that the spine 301 in the acquired ultrasound image 300 is at a 6 o'clock position (180 degrees) based on a comparison with the reference image 310. Referring again to FIG. 1, the ultrasound operator may instruct the fetal position processor 140 of the 6 o'clock spine position via the user input device 130.

Additionally and/or alternatively, the fetal position processor 140 may comprise suitable logic, circuitry, interfaces and/or code that may be operable to analyze acquired ultrasound images to automatically select a fetal position. For example, the fetal position processor 140 may include artificial intelligence image analysis algorithms, one or more deep neural networks (e.g., a convolutional neural network) and/or may utilize any suitable form of artificial intelligence image analysis techniques or machine learning processing functionality configured to analyze acquired ultrasound images to identify a fetal position (i.e., position and orientation). For example, the fetal position processor 140 may be provided as one or more deep neural networks that may be made up of, for example, an input layer, an output layer, and one or more hidden layers in between the input and output layers. Each of the layers may be made up of a plurality of processing nodes that may be referred to as neurons. For example, the fetal position processor 140 may include an input layer having a neuron for each pixel or a group of pixels from a scan plane of an anatomical structure. The output layer may have a neuron corresponding to a plurality of pre-defined fetal lies and/or spine orientations. As an example, if performing an ultrasound-based congenital heart disease examination, the output layer of one deep neural network may include neurons for a cephalic lie, a breech lie, and the like. The output layer of another deep neural network may include neurons for a spine at 3 o'clock (or 90 degrees), spine at 4 o'clock (or 120 degrees), spine at 5 o'clock (or 150 degrees), spine at 6 o'clock (or 180 degrees), spine at 7 o'clock (or 210 degrees), spine at 8 o'clock (or 240 degrees), spine at 9 o'clock (or 270 degrees), and the like. Other ultrasound procedures may utilize output layers that include neurons for positions and/or orientations of any suitable anatomical structure. Each neuron of each layer may perform a processing function and pass the processed ultrasound image information to one of a plurality of neurons of a downstream layer for further processing. As an example, neurons of a first layer may learn to recognize edges of structure in the ultrasound image data. The neurons of a second layer may learn to recognize shapes based on the detected edges from the first layer. The neurons of a third layer may learn positions of the recognized shapes relative to landmarks in the ultrasound image data. The processing performed by the fetal position processor 140 deep neural network (e.g., convolutional neural network) may identify a fetal (or other anatomical structure) position in ultrasound image data with a high degree of probability.

The fetal position processor 140 may be configured to determine the fetal position (i.e., position and orientation) based on the fetal lie, spine position, and/or any suitable fetal characteristic. The fetal position processor 140 may be configured to provide the fetal position information to a reference image processor 150 and/or store the fetal position information at archive 138 and/or any suitable data storage medium.

The signal processor 132 may include a reference image processor 150 that comprises suitable logic, circuitry, interfaces and/or code that may be operable to automatically select and present reference images based on the fetal position determined by the fetal position processor 140. The reference image processor 150 may select a corresponding set of reference images from the archive 138 and/or any suitable data storage medium based on the fetal position. Each set of reference images may include a different reference image for each view of an ultrasound examination. For example, a fetal congenital heart disease ultrasound examination may include sets of reference images each having a four chamber (4CH) view, a three vessel and trachea (3VT) view, left ventricular and right ventricular outflow tract views, short axis views (low for ventricles and high for outflow tracts), a long axis view, an aortic arch view, a ductal arch view, and superior and inferior vena cava views. Each set of reference images may correspond with a different fetal position, such as one set for cephalic lie and 6 o'clock spine position, one set for breech lie and 6 o'clock spine position, one set for cephalic lie and 5 o'clock spine position, one set for breech lie and 5 o'clock spine position, etc. The reference images may be pictograms and/or pre-acquired ultrasound images depicting each view of the examination procedure at the particular fetal position. In various embodiments, the reference images may include label of anatomical structures.

Additionally and/or alternatively, the reference image processor 150 may retrieve one set of reference images corresponding to a particular ultrasound examination and may rotate each of the reference images in the set based on the fetal position determined by the fetal position processor 140 to select the reference image set. For example, if the reference image set has a default fetal position of cephalic lie and spine at 6 o'clock and the fetal position determined by the fetal position processor 140 is breech lie at 6 o'clock, the reference image processor 150 may flip each reference image in the set over the horizontal axis and rotate each image 180 degrees to obtain an appropriate position and orientation for each reference image in the set.

The reference image processor 150 may be operable to present each image in the set of reference images sequentially. For example, after the fetal position is determined and the appropriate set of reference images is selected, the reference image processor 150 may present a first reference image (e.g., a 4CH view) at the display system 134. The ultrasound operator may manipulate the ultrasound probe 104 to acquire an image viewing plane that substantially matches the viewing plane of the reference image. The reference image processor 150 subsequently presents a next reference image (e.g., a 3VT view) at the display system 134. The reference image processor 150 continues presenting the reference images in this manner until the ultrasound operator acquires and/or analyzes ultrasound images corresponding with all of the reference image views. In various embodiments, an ultrasound operator may have an option to skip a reference image if desired, such as if the ultrasound operator is unable to manipulate the probe 104 to acquire the appropriate view despite the assistance provided by the presentation of the reference image.

Figure 4:
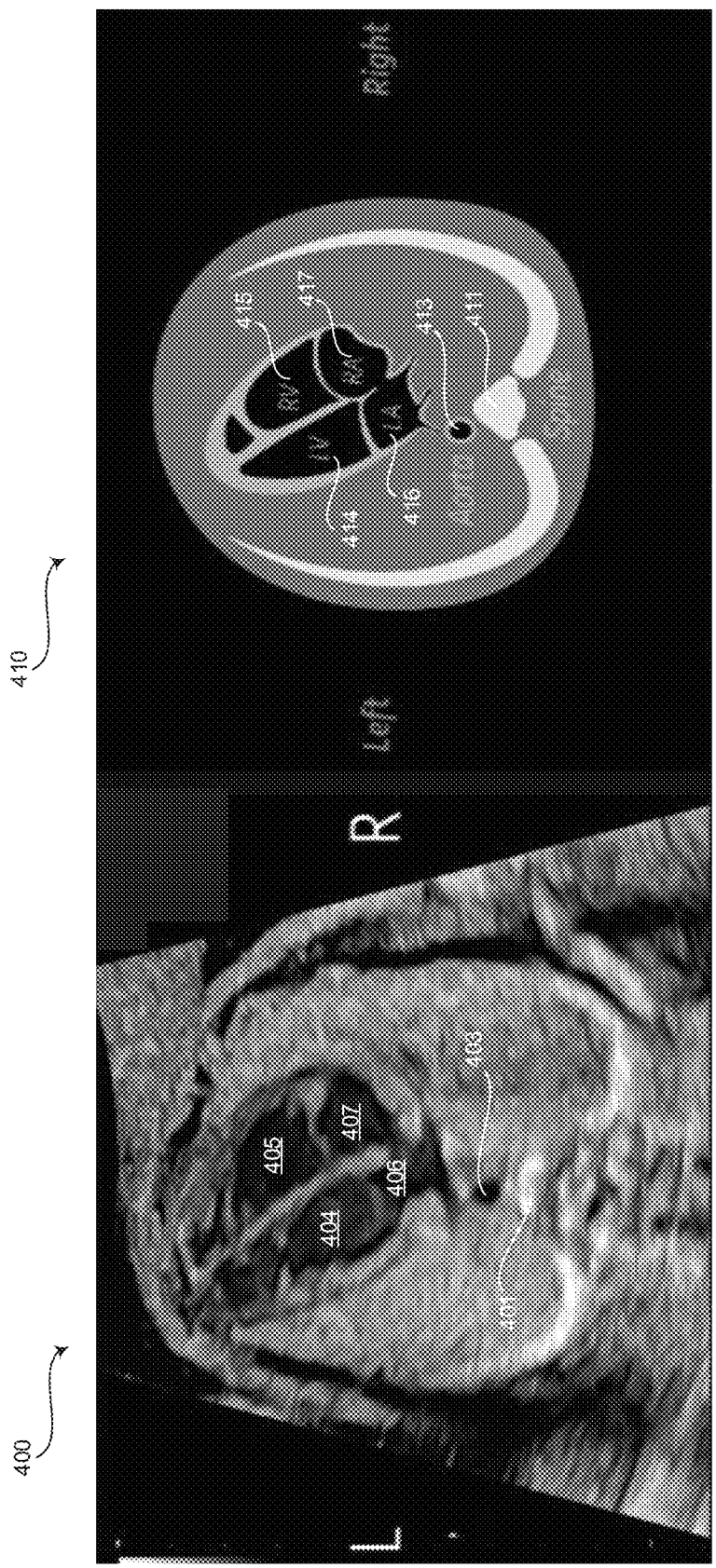
FIG. 4 is an exemplary display of an ultrasound image and reference image that may be used to assist acquisition of a four chamber (4CH) view in fetal ultrasound, in accordance with various embodiments.

FIG. 4 is an exemplary display of an ultrasound image 400 and reference image 410 that may be used to assist acquisition of a four chamber (4CH) view in fetal ultrasound, in accordance with various embodiments. Referring to FIG. 4, a reference image 410 of a 4CH view is shown. The reference image 410 may be a pictogram as shown in FIG. 4 or a pre-acquired ultrasound image. The reference image 410 may include labels, such as labels of the spine 411, aorta 413, left ventricle 414, right ventricle 415, left atria 416, right atria 417, ribs, and the like. The reference image 410 may include an identifier of the left and right sides of the image 410. The reference image 410 may be presented at a display system 134 of an ultrasound system 100 to assist an ultrasound operator with acquiring an ultrasound image 400 having a corresponding view (e.g., 4CH view). The ultrasound operator may manipulate an ultrasound probe 104 until an ultrasound image 400 having a substantially similar viewing plane is acquired. The acquired ultrasound image 400 of a 4CH view may include a spine 401, aorta 403, left ventricle 404, right ventricle 405, left atria 406, right atria 407, ribs, and the like.

Figure 5:
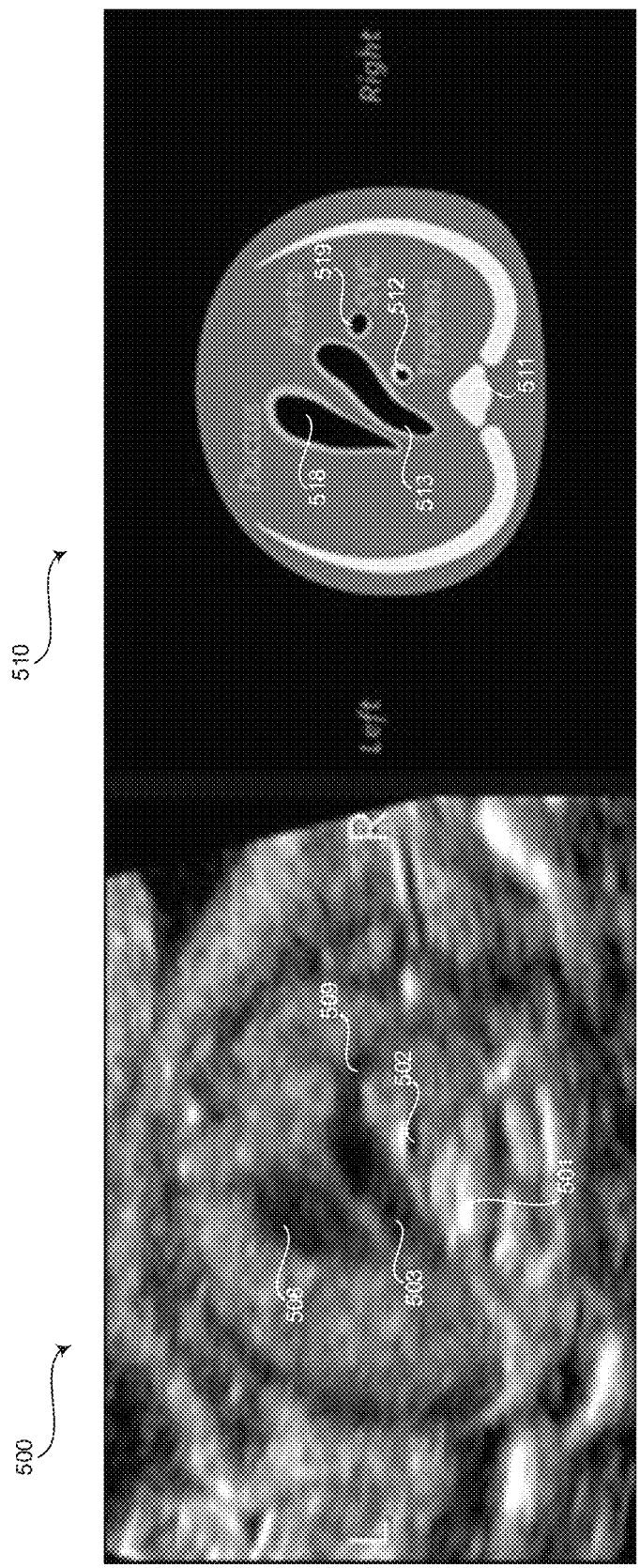
FIG. 5 is an exemplary display of an ultrasound image and reference image that may be used to assist acquisition of a three vessel and trachea (3VT) view in fetal ultrasound, in accordance with various embodiments.

FIG. 5 is an exemplary display of an ultrasound image 500 and reference image 510 that may be used to assist acquisition of a three vessel and trachea (3VT) view in fetal ultrasound, in accordance with various embodiments. Referring to FIG. 5, a reference image 510 of a 3VT view is shown. The reference image 510 may be a pictogram as shown in FIG. 5 or a pre-acquired ultrasound image. The reference image 510 may include labels, such as labels of the spine 511, trachea 512, aorta 513, ductus 518, superior vena cava (SVC) 519, ribs, and the like. The reference image 510 may include an identifier of the left and right sides of the image 510. The reference image 510 may be presented at a display system 134 of an ultrasound system 100 to assist an ultrasound operator with acquiring an ultrasound image 500 having a corresponding view (e.g., 3VT view). The ultrasound operator may manipulate an ultrasound probe 104 until an ultrasound image 500 having a substantially similar viewing plane is acquired. The acquired ultrasound image 500 of a 3VT view may include a spine 501, trachea 502, aorta 503, ductus 508, superior vena cava (SVC) 509, ribs, and the like.

Referring again to FIG. 1, the signal processor 132 may include an image feedback processor 160 that comprises suitable logic, circuitry, interfaces and/or code that may be operable to receive, generate, and/or display feedback regarding the acquired ultrasound images 300, 400, 500. For example, the image feedback processor 160 may be configured to automatically detect when an ultrasound image 300, 400, 500 matching a reference image 310, 410, 510 is acquired and provide an indication that the ultrasound probe 104 is correctly positioned. The indication may be a message (e.g., text, symbol, audio, probe vibration, etc.), adding an image view label to the ultrasound image, and/or any suitable indication. As another example, the image feedback processor 160 may be configured to prompt an ultrasound operator to answer questions presented at the display system 134. For example, the image feedback processor 160 may present a question asking whether the stomach is on the fetal left in a transverse abdominal view image, whether the apex points to the fetal left in a 4CH view image, or whether the orientation, size, and configuration of the structures match the reference image in a 3VT view image, among other things. The image feedback processor 160 may store the answers at the archive 138 and/or any suitable data storage medium and may present a summary of the examination based on the answers to the questions at the conclusion of the examination. For example, the image feedback processor 160 may provide a summary indicating whether each obtained ultrasound image view 300, 400, 500 is normal or abnormal based on the answers provided to the questions provided by the image feedback processor 160.

As another example, the image feedback processor 160 may comprise suitable logic, circuitry, interfaces and/or code that may be operable to analyze acquired ultrasound images 300, 400, 500 to automatically detect abnormal structures (e.g., malformations). For example, the image feedback processor 160 may include artificial intelligence image analysis algorithms, one or more deep neural networks (e.g., a convolutional neural network) and/or may utilize any suitable form of artificial intelligence image analysis techniques or machine learning processing functionality configured to analyze acquired ultrasound images to detect abnormalities (e.g., malformations). For example, the image feedback processor 160 may be provided as one or more deep neural networks that may be made up of, for example, an input layer, an output layer, and one or more hidden layers in between the input and output layers. Each of the layers may be made up of a plurality of processing nodes that may be referred to as neurons. For example, the image feedback processor 160 may include an input layer having a neuron for each pixel or a group of pixels from a scan plane of an anatomical structure. The output layer may have a neuron corresponding to a plurality of pre-defined conditions, such as normal and one or more various abnormalities. Each neuron of each layer may perform a processing function and pass the processed ultrasound image information to one of a plurality of neurons of a downstream layer for further processing. As an example, neurons of a first layer may learn to recognize edges of structure in the ultrasound image data 300, 400, 500. The neurons of a second layer may learn to recognize shapes based on the detected edges from the first layer. The neurons of a third layer may learn positions of the recognized shapes relative to landmarks in the ultrasound image data 300, 400, 500. The processing performed by the image feedback processor 160 deep neural network (e.g., convolutional neural network) may identify normal and abnormal anatomies in ultrasound image data with a high degree of probability.

The image feedback processor 160 may be operable to present the feedback at a display system 134 and/or store the generated feedback at the archive 138 or any suitable data storage medium.

Still referring to FIG. 1, the display system 134 may be any device capable of communicating visual information to a user. For example, a display system 134 may include a liquid crystal display, a light emitting diode display, and/or any suitable display or displays. The display system 134 may include one or more display screens. For example, the ultrasound image 300, 400, 500 may be presented at a first display screen of the display system 134 and the reference image 310, 410, 510 may be presented at a second display screen of the display system 134. The display system 134 can be operable to display information from the signal processor 132 and/or archive 138, such as ultrasound images 300, 400, 500, reference images 310, 410, 510, system prompts, examination summary information, and/or any suitable information.

The archive 138 may be one or more computer-readable memories integrated with the ultrasound system 100 and/or communicatively coupled (e.g., over a network) to the ultrasound system 100, such as a Picture Archiving and Communication System (PACS), a server, a hard disk, floppy disk, CD, CD-ROM, DVD, compact storage, flash memory, random access memory, read-only memory, electrically erasable and programmable read-only memory and/or any suitable memory. The archive 138 may include databases, libraries, sets of information, or other storage accessed by and/or incorporated with the signal processor 132, for example. The archive 138 may be able to store data temporarily or permanently, for example. The archive 138 may be capable of storing medical image data, data generated by the signal processor 132, and/or instructions readable by the signal processor 132, among other things. In various embodiments, the archive 138 stores ultrasound images 300, 400, 500, reference images 310, 410, 510, instructions for determining a fetal position, instructions for selecting a reference image, instructions for presenting system prompts, automated malformation detection instructions, and/or instructions for presenting an examination summary, among other things.

The training engine 170 may comprise suitable logic, circuitry, interfaces and/or code that may be operable to train the neurons of the deep neural network(s) of the fetal position processor 140 and/or the image feedback processor 160. For example, the artificial fetal position processor 140 and/or the image feedback processor 160 may be trained to automatically identify a fetal position and/or automatically detect anatomical structure abnormalities provided in an ultrasound scan plane. For example, the training engine 170 may train the deep neural networks of the fetal position processor 140 and/or the image feedback processor 160 using databases(s) of classified ultrasound images of various structures. As an example, the fetal position processor 140 and/or the image feedback processor 160 may be trained by the training engine 170 with ultrasound images of particular anatomical structures to train the fetal position processor 140 and/or the image feedback processor 160 with respect to the characteristics of the particular structure, such as the appearance of structure edges, the appearance of structure shapes based on the edges, the positions of the shapes relative to landmarks in the ultrasound image data, and the like. In an exemplary embodiment, the structures may include a fetal head, fetal spine, and/or any suitable organ, bone, nerve, vessel, tissue, or the like. The structural information may include information regarding the edges, shapes, and positions of the fetal head, fetal spine, organs, bones, nerves, vessels, tissue, and/or the like. In various embodiments, the databases of training images may be stored in the archive 138 or any suitable data storage medium. In certain embodiments, the training engine 170 and/or training image databases may be external system(s) communicatively coupled via a wired or wireless connection to the ultrasound system 100.

Components of the ultrasound system 100 may be implemented in software, hardware, firmware, and/or the like. The various components of the ultrasound system 100 may be communicatively linked. Components of the ultrasound system 100 may be implemented separately and/or integrated in various forms. For example, the display system 134 and the user input device 130 may be integrated as a touchscreen display.

Figure 6:
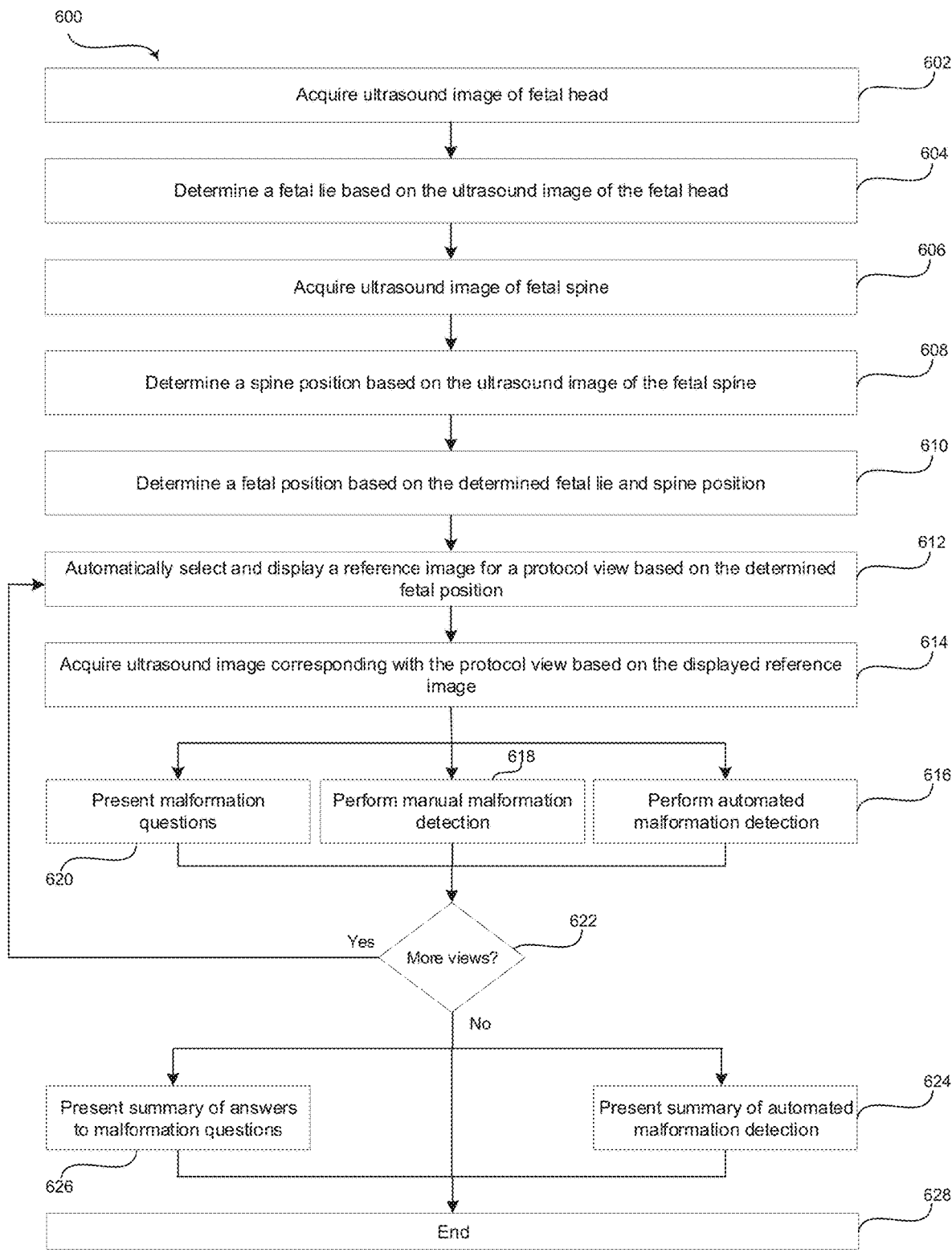
FIG. 6 is a flow chart illustrating exemplary steps that may be utilized for providing a guided workflow through a series of ultrasound image acquisitions with reference images updated based on a determined fetal position, in accordance with exemplary embodiments.

FIG. 6 is a flow chart 600 illustrating exemplary steps 602-628 that may be utilized for providing a guided workflow through a series of ultrasound image acquisitions with reference images updated based on a determined fetal position, in accordance with exemplary embodiments. Referring to FIG. 6, there is shown a flow chart 600 comprising exemplary steps 602 through 628. Certain embodiments may omit one or more of the steps, and/or perform the steps in a different order than the order listed, and/or combine certain of the steps discussed below. For example, some steps may not be performed in certain embodiments. As a further example, certain steps may be performed in a different temporal order, including simultaneously, than listed below.

At step 602, an ultrasound system 100 may acquire an ultrasound image of a fetal head. For example, an ultrasound operator may manipulate an ultrasound probe 104 of the ultrasound system 100 to obtain an ultrasound image of a fetal head. The ultrasound image may be presented by a signal processor 132 at a display system 134.

At step 604, a fetal lie is determined based on the ultrasound image of the fetal head. For example, a fetal position processor 140 of the signal processor 132 may determine the fetal lie based on a user instruction received via a user input device 130 or automatically based on artificial intelligence algorithms applied to the ultrasound image acquired at step 602. As an example, an ultrasound operator may analyze the ultrasound image acquired at step 602 (optionally with a reference image) and provide a selection, such as cephalic lie or breech lie, to the fetal position processor 140. As another example, the fetal position processor 140 may include artificial intelligence image analysis algorithms, one or more deep neural networks (e.g., a convolutional neural network) and/or may utilize any suitable form of artificial intelligence image analysis techniques or machine learning processing functionality configured to analyze the ultrasound image acquired at step 602 to determine the fetal lie.

At step 606, the ultrasound system 100 may acquire an ultrasound image 300 of a fetal spine 301. For example, the ultrasound operator may manipulate the ultrasound probe 104 of the ultrasound system 100 to a transverse abdominal view to obtain the ultrasound image 300 of a cross section of the thorax depicting the fetal spine 301. The ultrasound image may be presented by the signal processor 132 at the display system 134.

At step 608, a spine position is determined based on the ultrasound image 300 of the fetal spine 301. For example, a fetal position processor 140 of the signal processor 132 may determine the spine position based on a user instruction received via a user input device 130 or automatically based on artificial intelligence algorithms applied to the ultrasound image 300 acquired at step 606. As an example, an ultrasound operator may analyze the ultrasound image acquired at step 606 (optionally with a reference image 310) and provide a selection, such as spine at 3 o'clock (or 90 degrees), spine at 4 o'clock (or 120 degrees), spine at 5 o'clock (or 150 degrees), spine at 6 o'clock (or 180 degrees), spine at 7 o'clock (or 210 degrees), spine at 8 o'clock (or 240 degrees), spine at 9 o'clock (or 270 degrees), and/or any suitable spine position identifier, to the fetal position processor 140. As another example, the fetal position processor 140 may include artificial intelligence image analysis algorithms, one or more deep neural networks (e.g., a convolutional neural network) and/or may utilize any suitable form of artificial intelligence image analysis techniques or machine learning processing functionality configured to analyze the ultrasound image 300 acquired at step 606 to determine the spine position.

At step 610, the signal processor 132 may determine a fetal position (i.e., position and orientation) based on the determined fetal lie and spine position. For example, the fetal position processor 140 of the signal processor 132 may be operable to calculate the fetal position based on the fetal lie determined at step 604 and the spine position determined at step 608. The determined fetal position may be provided to the reference image processor 150 and/or stored in archive 138 or any suitable data storage medium.

At step 612, the signal processor 132 may automatically select and display a reference image 410, 510 for a protocol view based on the determined fetal position. For example, the reference image processor 150 may receive the fetal position determined at step 610 from the fetal position processor 140 and/or archive 138. The reference image processor 150 may select a set of reference images 410, 510 corresponding with a protocol based on the determined fetal position. For example, a set of reference images 410, 510 for each possible fetal position may be stored at archive 138 or any suitable data storage medium for selection and retrieval by the reference image processor 150. As another example, one set of reference images 410, 510 at a default fetal position may be stored at archive or any suitable data storage medium for retrieval by the reference image processor 150, which may rotate the reference images 410, 510 of the set from the default fetal position to the determined fetal position. The protocol may correspond with an examination type. For example, the protocol for a congenital heart disease fetal ultrasound examination may have a predetermined set of reference images 410, 510, including reference images for a 4CH view 410, a 3VT view 510, left ventricular and right ventricular outflow tract views, short axis views (low for ventricles and high for outflow tracts), a long axis view, an aortic arch view, a ductal arch view, and superior and inferior vena cava views. The reference image processor 150 may present each of the set of reference images 410, 510 based on the determined fetal position sequentially. For example, the reference image processor 150 may present a first of the set of reference images 410 at step 612. The process 600 may proceed to steps 614-622 and may return to step 612 if more views are available in the set of reference images 410, 510, where the next reference image 510 in the series is presented. The process repeats until all of the reference images 410, 510 have been presented at the display system 134 by the reference image processor 150.

At step 614, the ultrasound system 100 may acquire an ultrasound image 400, 500 corresponding with the protocol view based on the displayed reference image 410, 510. For example, the ultrasound operator may manipulate the ultrasound probe 104 of the ultrasound system 100 to acquire an ultrasound image 400, 500 that substantially matches the viewing plane of the reference image 410, 510. The ultrasound image 400, 500 may be presented by the signal processor 132 at the display system 134.

The process may then proceed to one of steps 616, 618, or 620.

At step 616, the signal processor 132 may perform automated malformation detection. For example, the image feedback processor 160 of the signal processor 132 may comprise artificial intelligence image analysis algorithms, one or more deep neural networks (e.g., a convolutional neural network) and/or may utilize any suitable form of artificial intelligence image analysis techniques or machine learning processing functionality configured to analyze acquired ultrasound images to detect abnormalities (e.g., malformations). The image feedback processor 160 may present any detected abnormalities (e.g., an alert message) and/or an indication of no detected abnormalities at step 616 and/or in an examination summary (e.g., a report) provided at step 624 as described below.

At step 618, an ultrasound operator may manually review and analyze the acquired ultrasound image to detect malformations. For example, an ultrasound operator may review and analyze the ultrasound image 400, 500 acquired at step 614 to determine whether any malformation or other abnormalities are present.

At step 620, the signal processor 132 of the ultrasound system 100 may present malformation questions. For example, the image feedback processor 160 may assist an ultrasound operator with malformation detection by providing one or more questions regarding the ultrasound image 400, 500 acquired at step 614. As an example, the image feedback processor 160 may provide a system prompt asking whether the stomach is on the fetal left in a transverse abdominal view image 300, whether the apex points to the fetal left in a 4CH view image 400, or whether the orientation, size, and configuration of the structures match the reference image in a 3VT view image 500, among other things. The image feedback processor 160 may provide feedback regarding potential abnormalities based on the answers to the questions at step 620 and/or in an examination summary provided at step 626 as described below.

At step 622, the signal processor 132 may determine whether ultrasound images 400, 500 corresponding to each protocol view in the set of reference images 410, 510 have been acquired by the ultrasound system 100. The process 600 may return to step 612 if additional ultrasound image views 400, 500 are to be acquired. The process 600 proceeds to step 624, 626, and/or 628 if no additional ultrasound image views 400, 500 are to be acquired.

At step 624, if automated malformation detection was performed at step 616, the signal processor 132 may present a summary of the automated malformation detection. For example, the image feedback processor 160 may present a summary at the display system 134 indicating whether each obtained ultrasound image view 300, 400, 500 is normal or abnormal based on the automated malformation detection provided by the image feedback processor 160 at step 616.

At step 626, the signal processor 132 may present a summary of the answers to the malformation questions presented at step 620. For example, the image feedback processor 160 of the signal processor 132 may provide a summary indicating whether each obtained ultrasound image view 300, 400, 500 is normal or abnormal based on the answers provided to the questions presented by the image feedback processor 160 at step 620.

At step 628, the process 600 ends.

Aspects of the present disclosure provide a method 600 and system 100 for providing a guided workflow through a series of ultrasound image acquisitions with reference images 410, 510 updated based on a determined anatomical position. In accordance with various embodiments, the method 600 may comprise acquiring and displaying 602, 606, by an ultrasound system 100, at least one ultrasound image 300 of an anatomy. The method 600 may comprise determining 604, 608, 610, by at least one processor 132, 140, a position of the anatomy depicted in the at least one ultrasound image 300. The method 600 may comprise automatically selecting and displaying 612, by the at least one processor 132, 150, reference images 410, 510 corresponding to pre-defined views of an ultrasound examination. An orientation of anatomy depicted in the selected and displayed reference images 410, 510 may be based on the determined position of the anatomy. The method 600 may comprise acquiring and displaying 614, by the ultrasound system 100, additional ultrasound images 400, 500 of the anatomy corresponding to the selected and displayed reference images 410, 510. The additional ultrasound images 400, 500 may have the pre-defined views of the ultrasound examination.

In a representative embodiment, the at least one ultrasound image 300 may comprise an ultrasound image of a fetal head and an ultrasound image 300 of a fetal spine 301. The at least one processor 132, 140 may determine the position of a fetus based on a fetal lie 200, 210 depicted in the ultrasound image of the fetal head and a spine position depicted in the ultrasound image 300 of the fetal spine 301. In an exemplary embodiment, one or both of the fetal lie 200, 210 and the spine position may be determined by the at least one processor 132, 140 executing at least one artificial intelligence image analysis algorithm or the at least one processor 132, 140 based on user instruction received via a user input device 130 selecting one or both the fetal lie 200, 210 and the spine position. In certain embodiments, the reference images 410, 510 are presented sequentially at a display system 134. In various embodiment, the reference images 410, 510 are one set of reference images 410, 510 in a plurality of sets of reference images. Each of the sets of reference images may have a different orientation corresponding to a different position of the anatomy. Alternatively, the reference images 410, 510 may be one set of reference images at a pre-defined orientation. The reference images 410, 510 may be rotated, by the at least one processor 132, 150, to the orientation based on the determined position of the anatomy. In a representative embodiment, the reference images 410, 510 may comprise one or both of a pictogram and a pre-acquired ultrasound image. In an exemplary embodiment, the method 600 may comprise automatically analyzing 616, by the at least one processor 132, 160, the additional ultrasound images 400, 500 to detect abnormalities of the anatomy depicted in the additional ultrasound images 400, 500. The method 600 may comprise generating 616, 624, by the at least one processor 132, 160, one or both of an alert and an examination summary based on the automated analysis of the additional ultrasound images 400, 500 for presentation at a display system 134. In certain embodiments, the method 600 may comprise presenting prompts of questions 620 with respect to an appearance of the additional ultrasound images 400, 500 compared to the reference images 410, 510. The method 600 may comprise receiving answers 620, by the at least one processor 132, 160, to the questions. The method 600 may comprise generating 620, 626, by the at least one processor 132, 160, one or both of an alert and an examination summary based on the received answers for presentation at a display system 134.

Various embodiments provide a system 100 for providing a guided workflow through a series of ultrasound image acquisitions with reference images 410, 510 updated based on a determined anatomical position. The system may comprise at least one processor 132, 140, 150, 160 and an ultrasound system 100 comprising an ultrasound probe 104, a display system 134, and the at least one processor 132, 140, 150, 160. The at least one processor 132, 140 may be configured to determine a position of anatomy depicted in at least one ultrasound image 300. The at least one processor 132, 150 may be configured to automatically select and display reference images 410, 510 corresponding to pre-defined views of an ultrasound examination. An orientation of anatomy depicted in the selected and displayed reference images 410, 510 may be based on the determined position of the anatomy. The ultrasound system 100 may be configured to acquire and display the at least one ultrasound image 300 of the anatomy at the display system 134. The ultrasound system 100 may be configured to acquire and display additional ultrasound images 400, 500 of the anatomy at the display system 134. The additional ultrasound images 400, 500 may correspond to the selected and displayed reference images 410, 510. The additional ultrasound images 400, 500 may have the pre-defined views of the ultrasound examination.

In an exemplary embodiment, the at least one ultrasound image 300 comprises an ultrasound image of a fetal head and an ultrasound image 300 of a fetal spine 301. The at least one processor 132, 140 may determine the position of a fetus based on a fetal lie 200, 210 depicted in the ultrasound image of the fetal head and a spine position depicted in the ultrasound image 300 of the fetal spine 301. The at least one processor 132, 140 may determine one or both of the fetal lie 200, 210 and the spine position by executing at least one artificial intelligence image analysis algorithm or receiving a user instruction via a user input device 130. The user instruction may select one or both the fetal lie 200, 210 and the spine position. In certain embodiments, the at least one processor 132, 150 may be configured to sequentially present the reference images 410, 510 at the display system 134. In various embodiments, the reference images 410, 510 may be one set of reference images 410, 510 in a plurality of sets of reference images. Each of the sets of reference images may have a different orientation corresponding to a different position of the anatomy. Alternatively, the reference images 410, 510 may be one set of reference images 410, 510 at a pre-defined orientation. The reference images 410, 510 may be rotated, by the at least one processor 132, 150, to the orientation based on the determined position of the anatomy. In a representative embodiment, the reference images 410, 510 may comprise a pictogram 410, 510 and/or a pre-acquired ultrasound image. In an exemplary embodiment, the at least one processor 132, 160 may be configured to automatically analyze the additional ultrasound images 400, 500 to detect abnormalities of the anatomy depicted in the additional ultrasound images 400, 500. The at least one processor 132, 160 may be configured to generate one or both of an alert and an examination summary based on the automated analysis of the additional ultrasound images 400, 500 for presentation at the display system 134. In various embodiments, the at least one processor 132, 160 may be configured to present prompts of questions with respect to an appearance of the additional ultrasound images compared to the reference images at the display system. The at least one processor 132, 160 may be configured to receive answers, via a user input device 130, to the questions. The at least one processor 132, 160 may be configured to generate one or both of an alert and an examination summary based on the received answers for presentation at the display system 134.

Certain embodiments provide a non-transitory computer readable medium having stored thereon, a computer program having at least one code section. The at least one code section is executable by a machine for causing the machine to perform steps 600. The steps 600 may comprise receiving and displaying 602, 606 at least one ultrasound image 400 of an anatomy. The steps 600 may comprise determining 604, 608, 610 a position of the anatomy depicted in the at least one ultrasound image 300. The steps 600 may comprise automatically selecting and displaying 612 reference images 410, 510 corresponding to pre-defined views of an ultrasound examination. An orientation of anatomy depicted in the selected and displayed reference images 410, 510 may be based on the determined position of the anatomy. The steps 600 may comprise receiving and displaying 614 additional ultrasound images 400, 500 of the anatomy corresponding to the selected and displayed reference images 410, 510. The additional ultrasound images 400, 500 may have the pre-defined views of the ultrasound examination.

In various embodiments, the at least one ultrasound image 300 may comprise an ultrasound image of a fetal head and an ultrasound image 300 of a fetal spine 301. In an exemplary embodiment, the steps 600 may comprise determining one or both of a fetal lie 200, 210 and a spine position by executing at least one artificial intelligence image analysis algorithm or receiving a user instruction selecting one or both the fetal lie 200, 210 and the spine position. The steps 600 may comprise determining the position of a fetus based on the fetal lie 200, 210 depicted in the ultrasound image of the fetal head and the spine position depicted in the ultrasound image 300 of the fetal spine 301. In a representative embodiment, the reference images 410, 510 may comprise one or both of a pictogram 410, 510 and a pre-acquired ultrasound image. In certain embodiments, the reference images 410, 510 are one set of reference images 410, 510 in a plurality of sets of reference images. Each of the sets of reference images having a different orientation corresponding to a different position of the anatomy. Alternatively, the reference images 410, 510 may be one set of reference images at a pre-defined orientation, and the steps 600 may comprise rotating the reference images 410, 510 to the orientation based on the determined position of the anatomy. In an exemplary embodiment, the steps 600 may comprise automatically analyzing 616 the additional ultrasound images 400, 500 to detect abnormalities of the anatomy depicted in the additional ultrasound images 400, 500. The steps 600 may comprise generating 616, 624 one or both of an alert and an examination summary based on the automated analysis of the additional ultrasound images 400, 500 for presentation at a display system 134. In certain embodiments, the steps 600 may comprise presenting prompts of questions 620 with respect to an appearance of the additional ultrasound images 400, 500 compared to the reference images 410, 510. The steps 600 may comprise receiving answers 620 to the questions. The steps 600 may comprise generating 620, 626 one or both of an alert and an examination summary based on the received answers for presentation at a display system 134.

As utilized herein the term "circuitry" refers to physical electronic components (i.e. hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, "and/or" means any one or more of the items in the list joined by "and/or". As an example, "x and/or y" means any element of the three-element set $\{(x), (y), (x, y)\}$. As another example, "x, y, and/or z" means any element of the seven-element set $\{(x), (y), (z), (x, y), (x, z), (y, z), (x, y, z)\}$. As utilized herein, the term "exemplary" means serving as a non-limiting example, instance, or illustration. As utilized herein, the terms "e.g.," and "for example" set off lists of one or more non-limiting examples, instances, or illustrations. As utilized herein, circuitry is "operable" or "configured" to perform a function whenever the circuitry comprises the necessary hardware and code (if any is necessary) to perform the function, regardless of whether performance of the function is disabled, or not enabled, by some user-configurable setting.

Other embodiments may provide a computer readable device and/or a non-transitory computer readable medium, and/or a machine readable device and/or a non-transitory machine readable medium, having stored thereon, a machine code and/or a computer program having at least one code section executable by a machine and/or a computer, thereby causing the machine and/or computer to perform the steps as described herein for providing a guided workflow through a series of ultrasound image acquisitions with reference images updated based on a determined anatomical position.

Accordingly, the present disclosure may be realized in hardware, software, or a combination of hardware and software. The present disclosure may be realized in a centralized fashion in at least one computer system, or in a distributed fashion where different elements are spread across several interconnected computer systems. Any kind of computer system or other apparatus adapted for carrying out the methods described herein is suited.

Various embodiments may also be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

While the present disclosure has been described with reference to certain embodiments, it will be understood by those skilled in the art that various changes may be made and equivalents may be substituted without departing from the scope of the present disclosure. In addition, many modifications may be made to adapt a particular situation or material to the teachings of the present disclosure without departing from its scope. Therefore, it is intended that the present disclosure not be limited to the particular embodiment disclosed, but that the present disclosure will include all embodiments falling within the scope of the appended claims.

What is claimed is:

1. A method comprising:
acquiring and displaying, by an ultrasound system, at least one ultrasound image of an anatomy;
determining, by at least one processor, a position of the anatomy depicted in the at least one ultrasound image;
automatically selecting and displaying, by the at least one processor, reference images corresponding to pre-defined views of an ultrasound examination, wherein an orientation of anatomy depicted in the selected and displayed reference images is based on the determined position of the anatomy; and
acquiring and displaying, by the ultrasound system, additional ultrasound images of the anatomy corresponding to the selected and displayed reference images, the additional ultrasound images having the pre-defined views of the ultrasound examination.

2. The method of claim 1, wherein the at least one ultrasound image comprises an ultrasound image of a fetal head and an ultrasound image of a fetal spine, and wherein the at least one processor determines the position of a fetus based on a fetal lie depicted in the ultrasound image of the fetal head and a spine position depicted in the ultrasound image of the fetal spine.

3. The method of claim 2, wherein one or both of the fetal lie and the spine position is determined by one of:
the at least one processor executing at least one artificial intelligence image analysis algorithm; or
the at least one processor based on user instruction received via a user input device selecting one or both the fetal lie and the spine position.

4. The method of claim 1, wherein the reference images are presented sequentially at a display system.

5. The method of claim 1, wherein one of:
the reference images are one set of reference images in a plurality of sets of reference images, each of the sets of reference images having a different orientation corresponding to a different position of the anatomy; or
the reference images are one set of reference images at a pre-defined orientation, wherein the reference images are rotated, by the at least one processor, to the orientation based on the determined position of the anatomy.

6. The method of claim 1, wherein the reference images comprise one or both of a pictogram and a pre-acquired ultrasound image.

7. The method of claim 1, comprising:
automatically analyzing, by the at least one processor, the additional ultrasound images to detect abnormalities of the anatomy depicted in the additional ultrasound images; and
generating, by the at least one processor, one or both of an alert and an examination summary based on the automated analysis of the additional ultrasound images for presentation at a display system.

8. The method of claim 1, comprising:
presenting prompts of questions with respect to an appearance of the additional ultrasound images compared to the reference images;
receiving answers, by the at least one processor, to the questions; and
generating, by the at least one processor, one or both of an alert and an examination summary based on the received answers for presentation at a display system.

9. A system comprising:
at least one processor configured to:
determine a position of anatomy depicted in at least one ultrasound image; and
automatically select and display reference images corresponding to pre-defined views of an ultrasound examination, wherein an orientation of anatomy depicted in the selected and displayed reference images is based on the determined position of the anatomy; and
an ultrasound system comprising an ultrasound probe, a display system, and the at least one processor, the ultrasound system configured to:
acquire and display the at least one ultrasound image of the anatomy at the display system; and
acquire and display additional ultrasound images of the anatomy at the display system, the additional ultrasound images corresponding to the selected and displayed reference images, the additional ultrasound images having the pre-defined views of the ultrasound examination.

10. The system of claim 9, wherein:
the at least one ultrasound image comprises an ultrasound image of a fetal head and an ultrasound image of a fetal spine;
the at least one processor determines the position of a fetus based on a fetal lie depicted in the ultrasound image of the fetal head and a spine position depicted in the ultrasound image of the fetal spine; and
the at least one processor determines one or both of the fetal lie and the spine position by one of:
executing at least one artificial intelligence image analysis algorithm; or
receiving a user instruction via a user input device, the user instruction selecting one or both the fetal lie and the spine position.

11. The system of claim 9, wherein the at least one processor is configured to sequentially present the reference images at the display system.

12. The system of claim 9, wherein one of:
the reference images are one set of reference images in a plurality of sets of reference images, each of the sets of reference images having a different orientation corresponding to a different position of the anatomy; or
the reference images are one set of reference images at a pre-defined orientation, wherein the reference images are rotated, by the at least one processor, to the orientation based on the determined position of the anatomy.

13. The system of claim 9, wherein the reference images comprise one or both of a pictogram and a pre-acquired ultrasound image.

14. The system of claim 9, wherein the at least one processor is configured to:
   automatically analyze the additional ultrasound images to detect abnormalities of the anatomy depicted in the additional ultrasound images; and
   generate one or both of an alert and an examination summary based on the automated analysis of the additional ultrasound images for presentation at the display system.

15. The system of claim 9, wherein the at least one processor is configured to:
   present prompts of questions with respect to an appearance of the additional ultrasound images compared to the reference images at the display system;
   receive answers, via a user input device, to the questions; and
   generate one or both of an alert and an examination summary based on the received answers for presentation at the display system.

16. A non-transitory computer readable medium having stored thereon, a computer program having at least one code section, the at least one code section being executable by a machine for causing the machine to perform steps comprising:
   receiving and displaying at least one ultrasound image of an anatomy;
   determining a position of the anatomy depicted in the at least one ultrasound image;
   automatically selecting and displaying reference images corresponding to pre-defined views of an ultrasound examination, wherein an orientation of anatomy depicted in the selected and displayed reference images is based on the determined position of the anatomy; and
   receiving and displaying additional ultrasound images of the anatomy corresponding to the selected and displayed reference images, the additional ultrasound images having the pre-defined views of the ultrasound examination.

17. The non-transitory computer readable medium of claim 16, wherein the at least one ultrasound image comprises an ultrasound image of a fetal head and an ultrasound image of a fetal spine, and comprising:
   determining one or both of a fetal lie and a spine position by one of:
      executing at least one artificial intelligence image analysis algorithm; or
      receiving a user instruction selecting one or both the fetal lie and the spine position; and
   determining the position of a fetus based on the fetal lie depicted in the ultrasound image of the fetal head and the spine position depicted in the ultrasound image of the fetal spine.

18. The non-transitory computer readable medium of claim 16, wherein the reference images comprise one or both of a pictogram and a pre-acquired ultrasound image, and wherein one of:
   the reference images are one set of reference images in a plurality of sets of reference images, each of the sets of reference images having a different orientation corresponding to a different position of the anatomy; or
   the reference images are one set of reference images at a pre-defined orientation, and comprising rotating the reference images to the orientation based on the determined position of the anatomy.

19. The non-transitory computer readable medium of claim 16, comprising:
   automatically analyzing the additional ultrasound images to detect abnormalities of the anatomy depicted in the additional ultrasound images; and
   generating one or both of an alert and an examination summary based on the automated analysis of the additional ultrasound images for presentation at a display system.

20. The non-transitory computer readable medium of claim 16, comprising:
   presenting prompts of questions with respect to an appearance of the additional ultrasound images compared to the reference images;
   receiving answers to the questions; and
   generating one or both of an alert and an examination summary based on the received answers for presentation at a display system.

* * * * *